US010889620B2

United States Patent
Eidelman et al.

(10) Patent No.: US 10,889,620 B2
(45) Date of Patent: Jan. 12, 2021

(54) SOLID STATE FORMS OF LINACLOTIDE

(71) Applicant: NOVETIDE LTD., Haifa Bay (IL)

(72) Inventors: Chaim Eidelman, D.N. Oshrat (IL); Hagi Alon, D.N. (IL); Dov Vayer, Haifa (IL); Sharon Penias-Navon, Kyriat Ata (IL); Jonathan Enav, Bnei-Brak (IL)

(73) Assignee: NOVETIDE LTD., Haifa Bay (IL)

( * ) Notice: Subject to any disclaimer, the term of this patent is extended or adjusted under 35 U.S.C. 154(b) by 0 days.

(21) Appl. No.: 15/740,856

(22) PCT Filed: Jul. 1, 2016

(86) PCT No.: PCT/US2016/040676
§ 371 (c)(1),
(2) Date: Dec. 29, 2017

(87) PCT Pub. No.: WO2017/004510
PCT Pub. Date: Jan. 5, 2017

(65) Prior Publication Data
US 2019/0194256 A1 Jun. 27, 2019

Related U.S. Application Data

(60) Provisional application No. 62/193,336, filed on Jul. 16, 2015, provisional application No. 62/187,479, filed on Jul. 1, 2015.

(51) Int. Cl.
*C07K 7/54* (2006.01)
*C07K 7/08* (2006.01)

(52) U.S. Cl.
CPC ............. *C07K 7/54* (2013.01); *C07K 7/08* (2013.01); *C07B 2200/13* (2013.01)

(58) Field of Classification Search
None
See application file for complete search history.

(56) References Cited

U.S. PATENT DOCUMENTS

| 7,304,036 | B2 | 12/2007 | Currie et al. |
| 7,371,727 | B2 | 5/2008 | Currie et al. |
| 8,222,201 | B2 | 7/2012 | Sanghvi et al. |
| 8,293,704 | B2 | 10/2012 | Sanghvi et al. |
| 2012/0214750 | A1* | 8/2012 | Sanghvi .................. A61P 1/00 514/21.1 |

FOREIGN PATENT DOCUMENTS

| WO | 2014118180 A1 | 8/2014 |
| WO | 2014188011 A2 | 11/2014 |

OTHER PUBLICATIONS

International Search Report for International Application No. PCT/US2016/040676, International Filing Date Jul. 1, 2016, dated Jan. 12, 2017, 5 pages.
Written Opinion for International Application No. PCT/US2016/040676, International Filing Date Jul. 1, 2016, dated Jan. 12, 2017, 8 pages.
Gongora-Benitez, Miriam et al.; "Optimized Fmoc Solid-Phase Synthesis of the Cysteine-Rich Peptide Linaclotide"; Biopolymers (PeptideScience), vol. 96, No. 1: 2010; pp. 69-80.

\* cited by examiner

*Primary Examiner* — Christina Bradley
(74) *Attorney, Agent, or Firm* — Cantor Colburn LLP

(57) ABSTRACT

Solid state forms of Linaclotide, processes for their preparation, compositions comprising them and medical uses thereof are provided. The solid state forms of Linaclotide are useful in the preparation of other solid state forms of Linaclotide, particularly the amorphous form.

11 Claims, 11 Drawing Sheets

Specification includes a Sequence Listing.

Figure 1: X-ray powder diffractograms of Linaclotide Form III
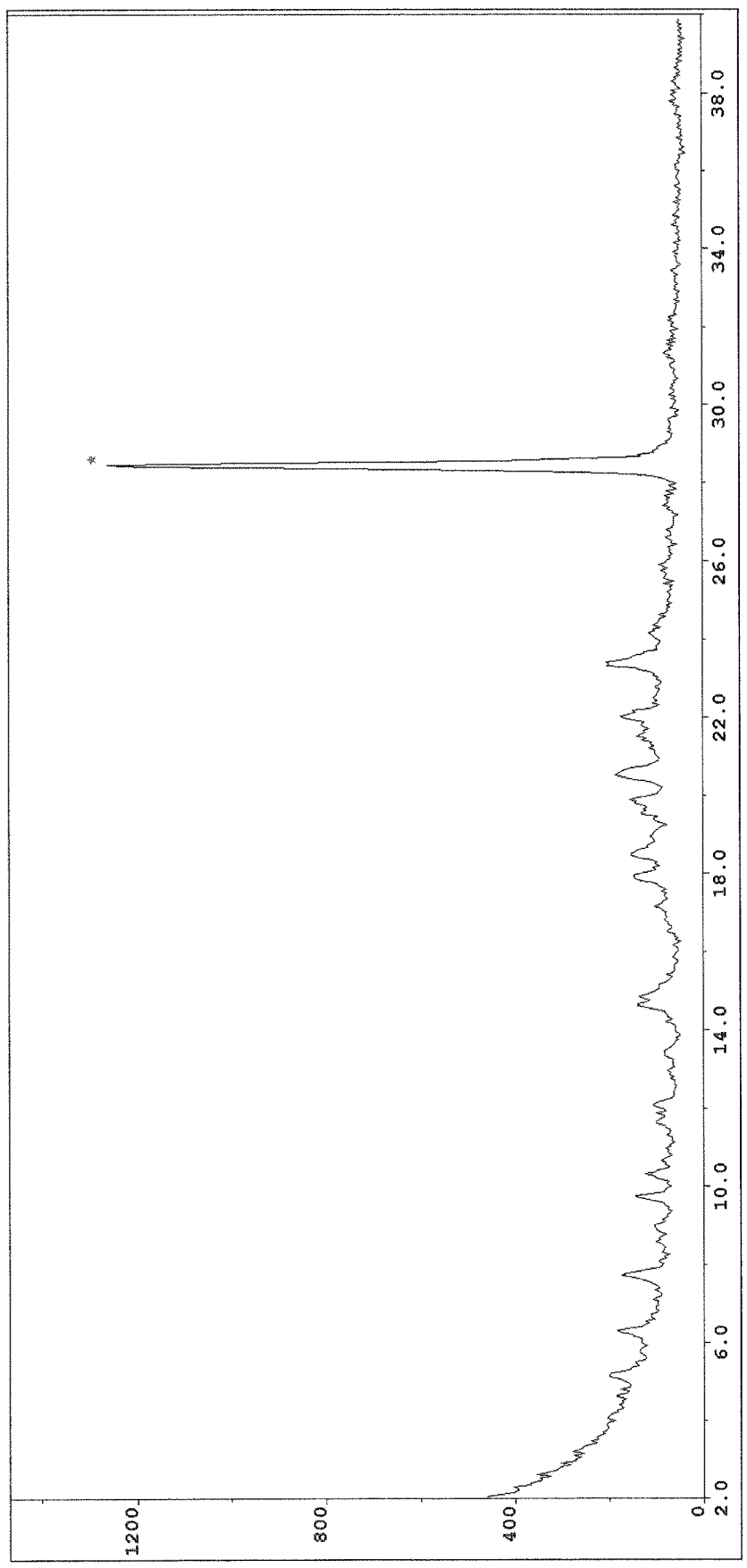
*The peak marked by star relates to addition of Silicon internal standard.

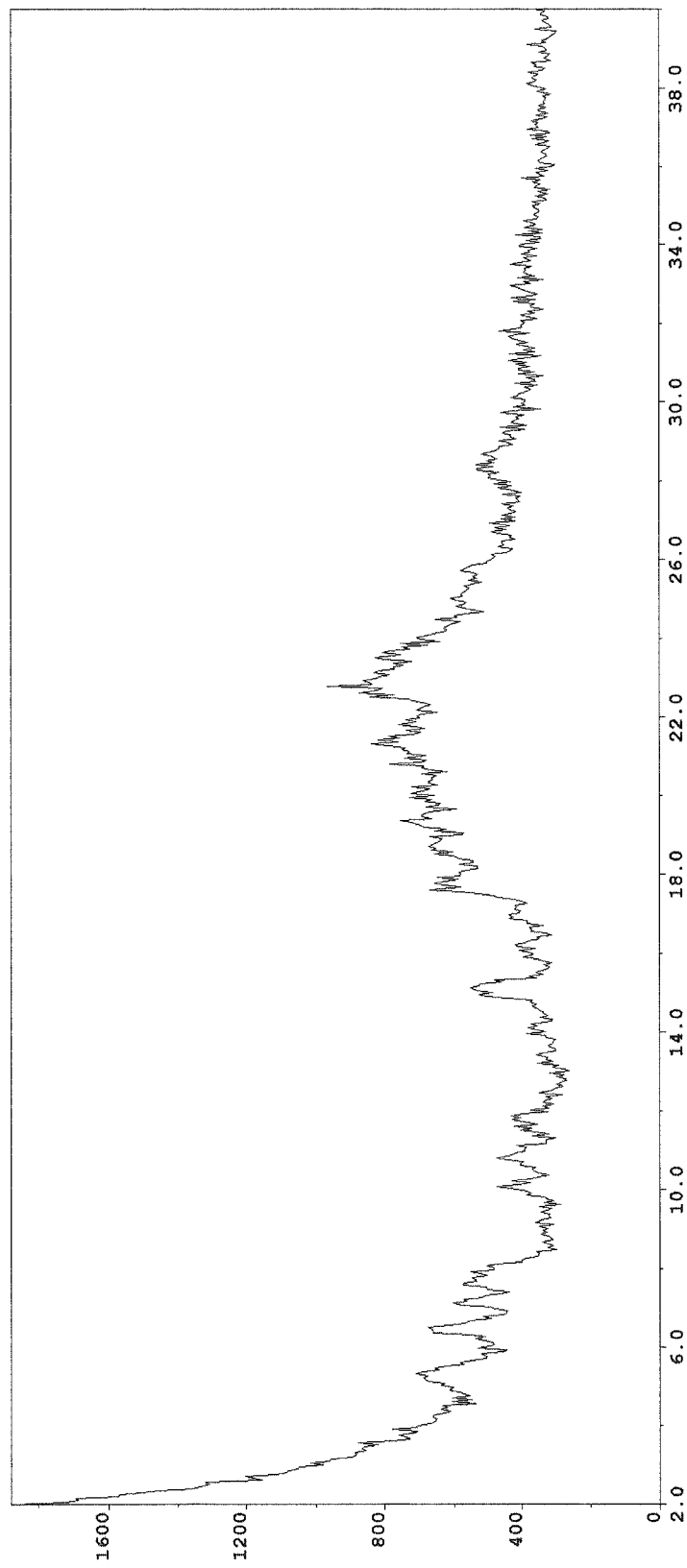
Figure 2: An X-ray powder diffractogram of Linaclotide Form IV

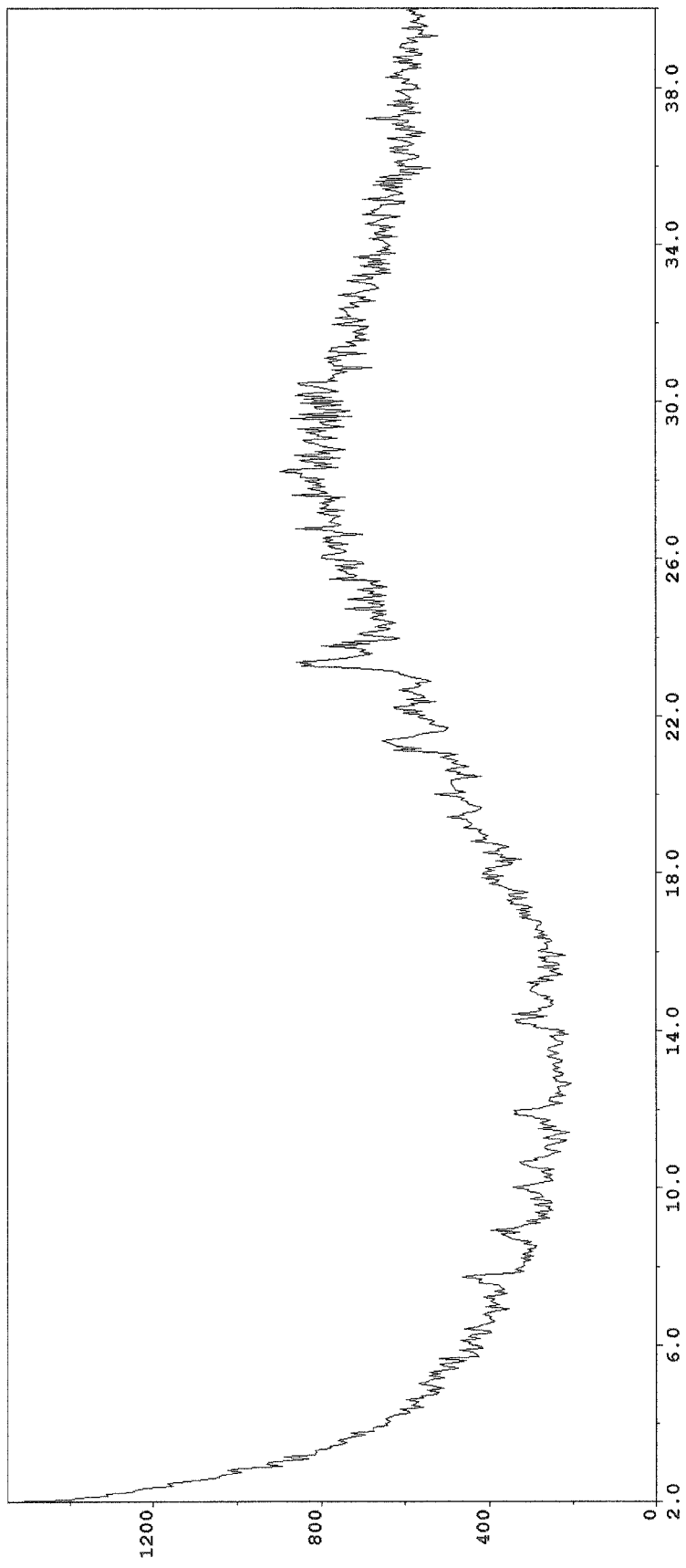
Figure 3: An X-ray powder diffractogram of Linaclotide Form V

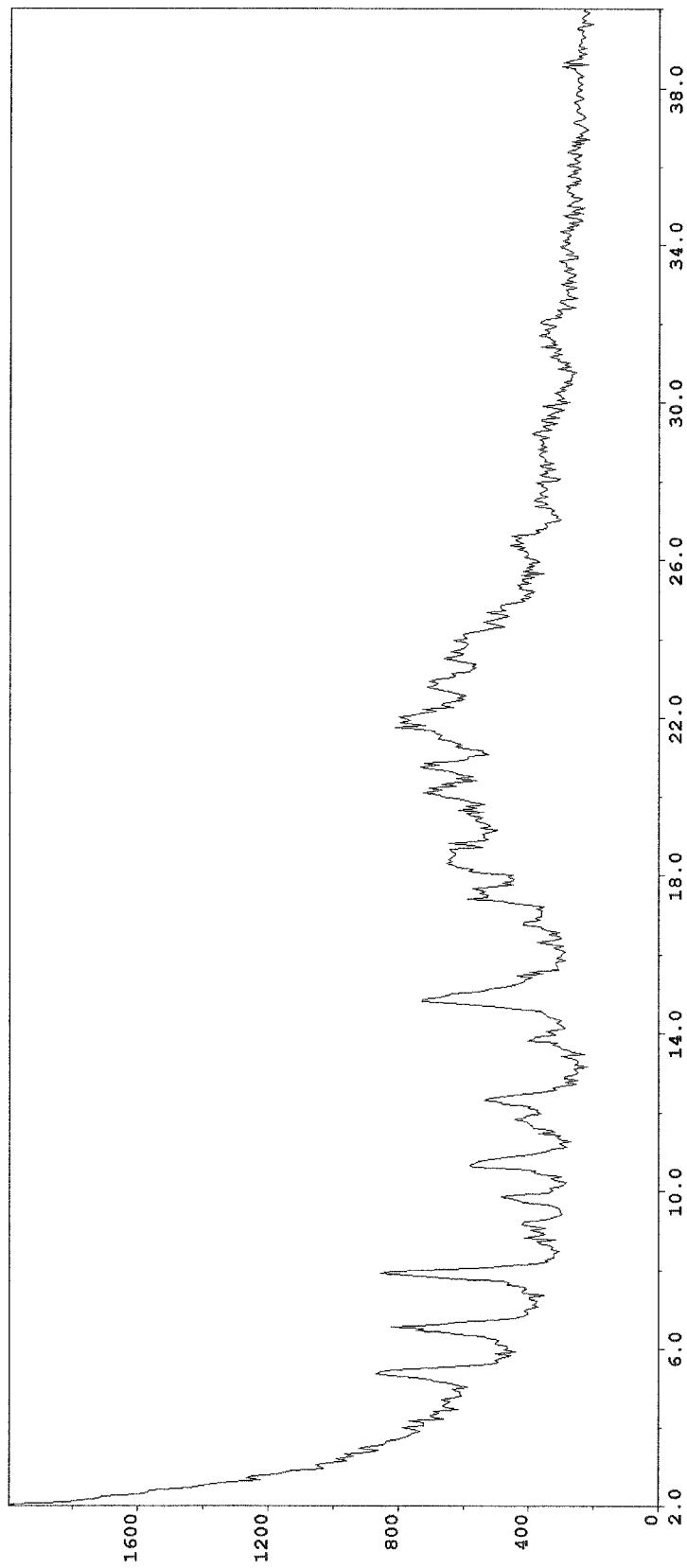
Figure 4: An X-ray powder diffractogram of Linaclotide Form VI

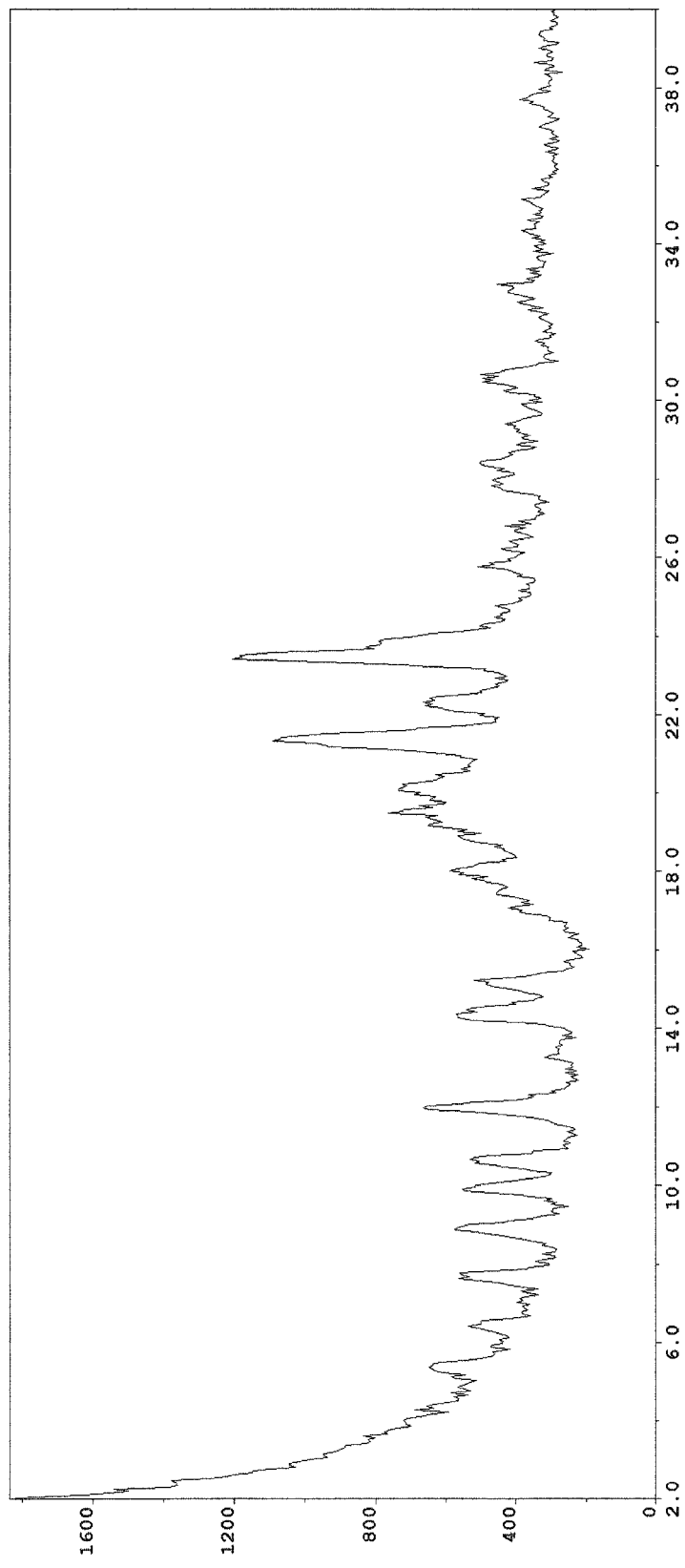
Figure 5: An X-ray powder diffractogram of Linaclotide Form VII

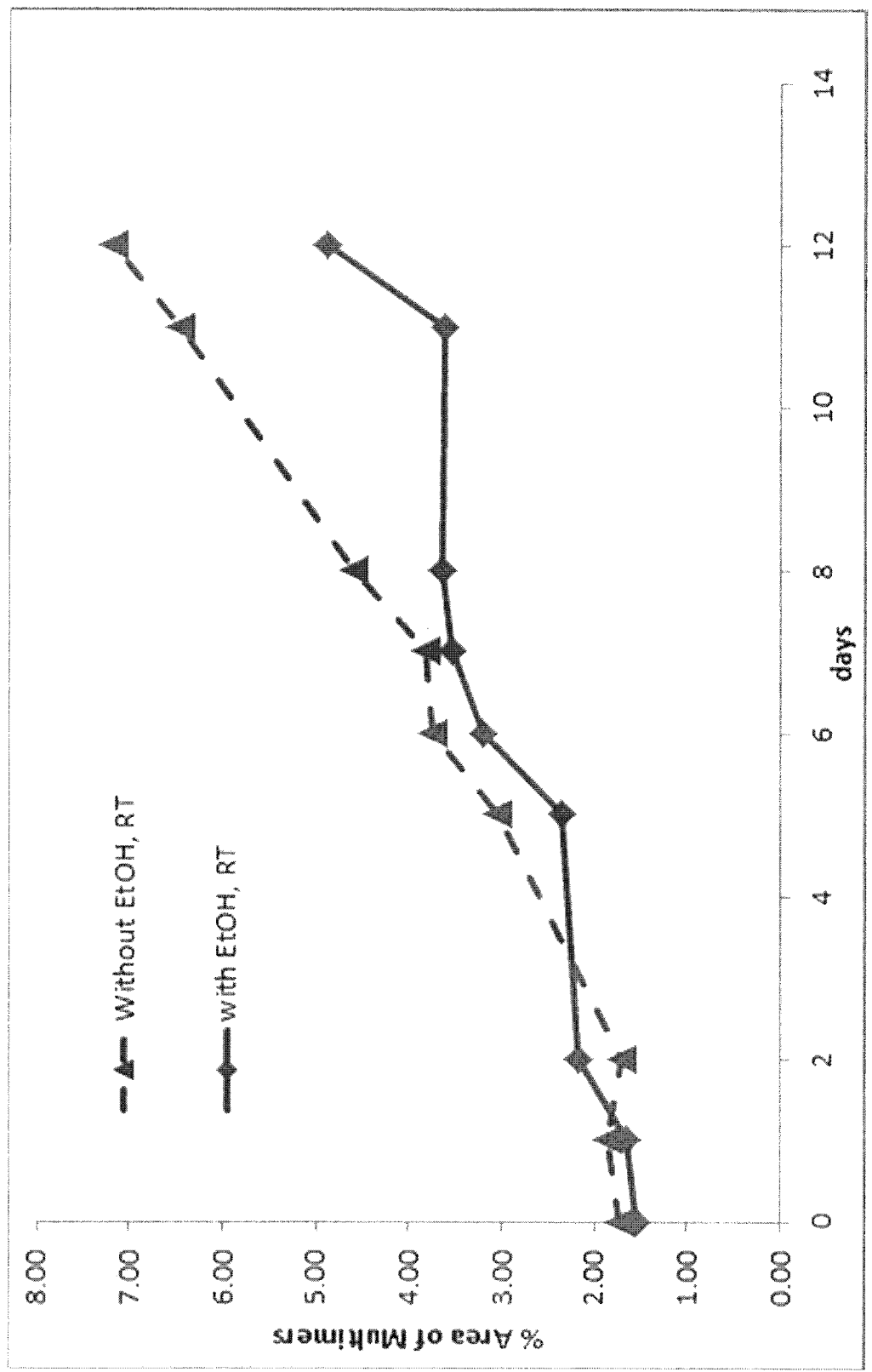
Figure 6: Stability of Linaclotide Solutions With/Without Ethanol

Figures 7A and 7B: Microscope images of Linaclotide Form III

Figures 8A and 8B: Microscope images of Amorphous Linaclotide

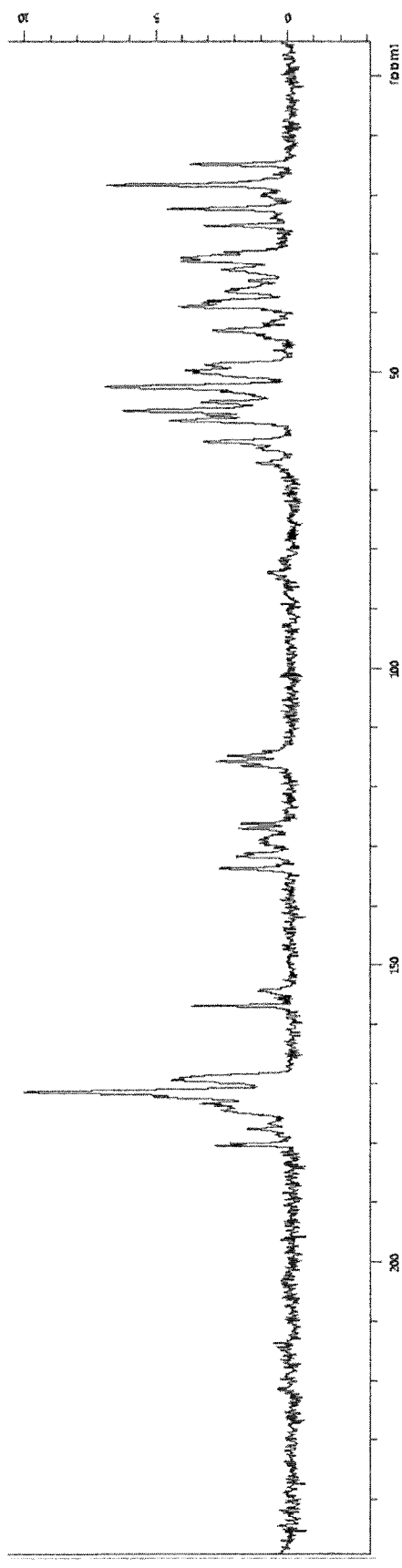
Figure 9: Solid State $^{13}$C NMR of Linaclotide Form III
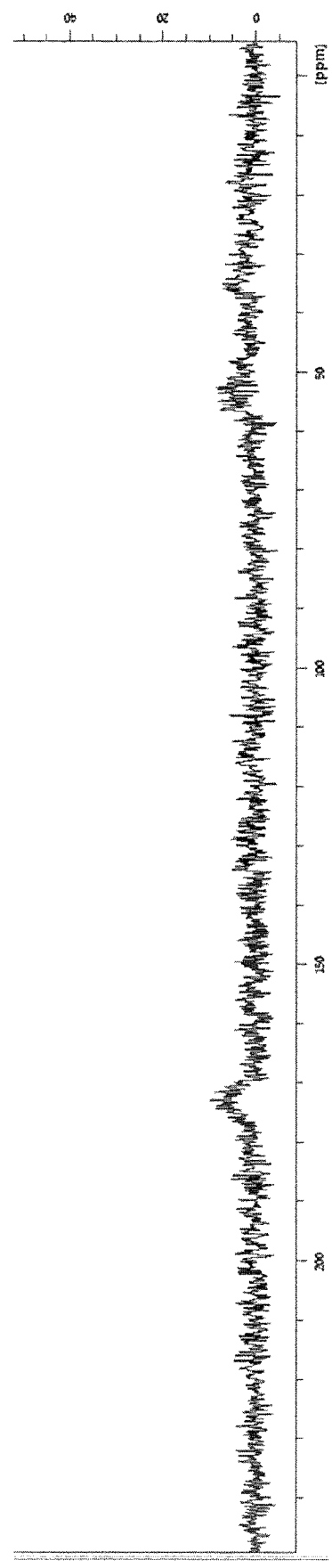
Figure 10: Solid State $^{13}$C NMR of Amorphous Linaclotide

SOLID STATE FORMS OF LINACLOTIDE

CROSS-REFERENCE TO RELATED APPLICATIONS

This application is a National Stage application of PCT/US2016/040676, filed 1 Jul. 2016, which claims priority to U.S. Provisional Application No. 62/187,479, filed 1 Jul. 2015, and to United States Provisional Application No. 62/193,336, filed 16 Jul. 2015. The disclosure of each of these applications is incorporated herein by reference in its entirety for all purposes.

SEQUENCE LISTING

A Sequence Listing, incorporated herein by reference, is submitted in electronic form as an ASCII text file, created Dec. 9, 2019, of size 4 KB and named "8FY2424.TXT".

FIELD OF THE INVENTION

The present invention encompasses novel solid state forms of Linaclotide, processes for their preparation, compositions comprising them and medical uses thereof. The present invention also encompasses the novel solid state forms of Linaclotide for use in the preparation of other solid state forms of Linaclotide, particularly amorphous form.

BACKGROUND OF THE INVENTION

Linaclotide is a 14-amino-acid cyclic peptide, which consists of the following amino acid sequence: Cys Cys Glu Tyr Cys Cys Asn Pro Ala Cys Thr Gly Cys Tyr (SEQ ID NO:1) with three disulfide bonds at positions 1 and 6, 2 and 10, and 5 and 13.

U.S. Pat. No. 7,304,036 discloses linaclotide and its activity as agonist of the guanylate cyclase C (GC-C) receptor for the treatment of gastrointestinal disorders.

U.S. Pat. Nos. 8,222,201 and 8,293,704 describe crystalline forms of Linaclotide. These publications also disclose that amorphous Linaclotide is obtained following the procedure described in U.S. Pat. Nos. 7,304,036 and 7,371,727.

In addition, WO2014118180 describes polymorphic Form II of Linaclotide.

Polymorphism, the occurrence of different crystalline forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray diffraction pattern, infrared absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new salts, solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life (chemical/physical stability). For at least these reasons, there is a need for additional salts and solid state forms (including solvated forms) of Linaclotide.

SUMMARY OF THE INVENTION

The present invention provides solid state forms of Linaclotide and pharmaceutical compositions thereof.

The present invention provides solid state forms of Linaclotide for use in the preparation of pharmaceutical compositions and/or formulations of this compound.

The present invention also encompasses the use of the solid state forms of Linaclotide of the present invention for the preparation of pharmaceutical compositions and/or formulations of this compound.

The present invention comprises a process for preparing the above mentioned pharmaceutical formulations. The process comprises combining the Linaclotide with at least one pharmaceutically acceptable excipient.

The Linaclotide forms, and the pharmaceutical compositions and/or formulations of the present invention can be used as medicaments, particularly for the treatment of gastrointestinal disorders.

The present invention further provides Linaclotide for use in the preparation of other solid state forms of Linaclotide, particularly amorphous form.

BRIEF DESCRIPTION OF THE DRAWINGS

FIG. 1 shows an X-ray powder diffractogram of Linaclotide Form III

FIG. 2 shows an X-ray powder diffractogram of Linaclotide Form IV

FIG. 3 shows an X-ray powder diffractogram of Linaclotide Form V

FIG. 4 shows an X-ray powder diffractogram of Linaclotide Form VI

FIG. 5 shows an X-ray powder diffractogram of Linaclotide Form VII

FIG. 6 shows the results of stability of Linaclotide solutions with and without ethanol FIG. 9 shows a solid state $^{13}$C NMR of Linaclotide Form III FIG. 10 shows a solid state $^{13}$C NMR of Amorphous Linaclotide

DETAILED DESCRIPTION OF THE INVENTION

Figure 7A:
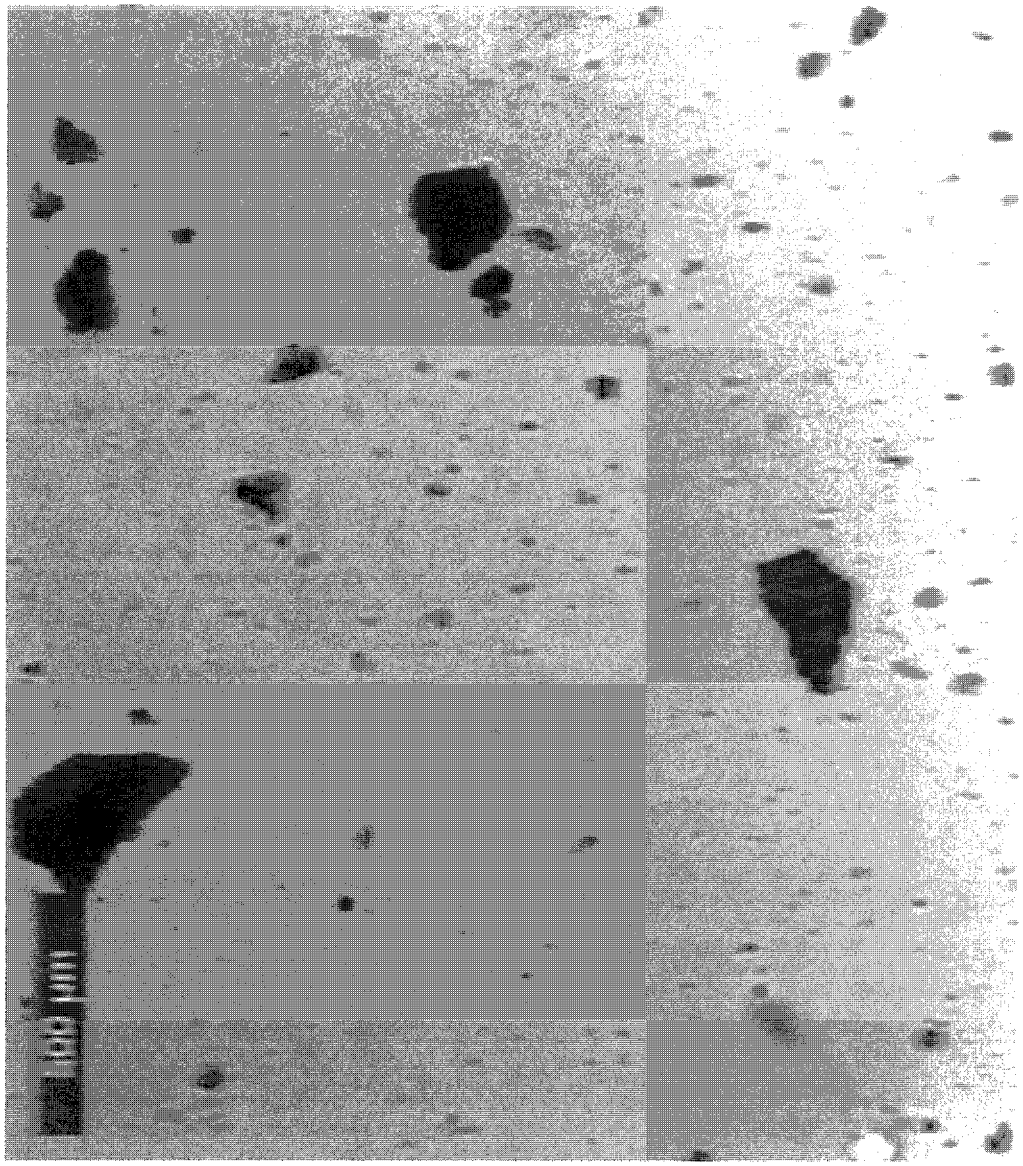
FIGS. 7A and 7B show microscope images of Linaclotide Form III

The present invention encompasses solid state forms of Linaclotide. Solid state properties of Linaclotide can be influenced by controlling the conditions under which the Linaclotide is obtained in solid form.

In some embodiments, the solid state forms of Linaclotide of the invention are substantially free of any other forms of Linaclotide.

Depending on which other solid state forms comparison is made with, the crystalline forms of Linaclotide of the present invention have advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of a Linaclotide referred to herein as being characterized by graphical data "as depicted in" or "as substantially depicted in" a Figure will thus be understood to include any crystal forms of Linaclotide characterized with the graphical data having such small variations, as are well known to the skilled person, in comparison with the Figure.

As used herein, the term "isolated" in reference to solid state form of Linaclotide of the present invention corresponds to a solid state form of Linaclotide that is physically separated from the reaction mixture in which it is formed.

As used herein, "substantially free" is meant that the solid state forms of Linaclotide contain about 20% (w/w) or less of polymorphs, or of a specified polymorph of Linaclotide. According to some embodiments, the solid state forms of the present disclosure contain about 10% (w/w) or less, about 5% (w/w) or less, about 2% (w/w) or less, about 1% (w/w) or less, about 0.5% (w/w) or less, or about 0.2% (w/w) or less of polymorphs, or of a specified polymorph of Linaclotide. In other embodiments, solid state forms of Linaclotide of the present disclosure contain from about 1% to about 20% (w/w), from about 5% to about 20% (w/w), or from about 5% to about 10% (w/w) of any solid state forms or of a specified polymorph of Linaclotide.

As used herein, unless stated otherwise, the XRPD measurements are taken using copper Kα radiation wavelength 1.5418 Å.

As used herein, unless stated otherwise, solid state $^{13}$C NMR is obtained at 125 MHz, with magic angle spinning rate of 11 kHz.

As used herein, optical microscopy was conducted with a light microscope, with the sample suspended in light mineral oil and dispersed on a glass slide.

As used herein, L-Asp Linaclotide impurity (also referred to herein as Linaclotide hydrolysis product) refers to Linaclotide impurity wherein the Asn residue of Linaclotide has been hydrolysed to Asp.

As used herein, acetylated Linaclotide impurity refers to Linaclotide wherein the N-terminus (i.e. the $Cys^1$ residue) is acetylated.

As used herein, multimers refer to Linaclotide oligomers formed via connection of two or more monomeric units of Linaclotide through one or more disulfide (S—S) bonds.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 100 mbar.

As used herein, and unless indicated otherwise, the terms "wet crystalline form" or "wet form" refer to a polymorph that was not dried using any conventional techniques to remove residual solvent. Examples for such conventional techniques can be, but not limited to, evaporation, vacuum drying, oven drying, drying under nitrogen flow etc.

As used herein, and unless indicated otherwise, the terms "dry crystalline form" or "dry form" refer to a polymorph that was dried using any conventional techniques to remove residual solvent. Examples for such conventional techniques can be, but not limited to, evaporation, vacuum drying, oven drying, drying under nitrogen flow etc.

In a first embodiment, the present invention comprises crystalline Form III of Linaclotide characterized by data selected from one or more of the following: an X-ray powder diffraction pattern having peaks at 5.1, 7.7, 10.3, 14.8 and 22.0 degrees two theta ±0.2 degrees two theta; or an X-ray powder diffraction pattern as depicted in FIG. 1; or a solid state $^{13}$C NMR having peaks at 18.5, 43.0, 49.9, 52.4, 56.5, 61.9, 115.7, 133.8, 169.1, 171.5±2 ppm; or combinations of this data.

In one embodiment, the present invention comprises crystalline Linaclotide, designated form III, characterized by data selected from one or more of the following: X-ray powder diffraction pattern having peaks at 5.1, 7.7, 10.3, 14.8 and 22.0 degrees two theta ±0.2 degrees two theta; an X-ray powder diffraction pattern as depicted in FIG. 1; and combinations of this data.

Crystalline form III of Linaclotide can be further characterized by the X-ray powder diffraction pattern having peaks at 5.1, 7.7, 10.3, 14.8 and 22.0 degrees two theta ±0.2 degrees two theta and also having any one, any two, any three or more additional peaks selected from: 6.3, 9.7, 17.9, 20.6 and 23.4 two theta ±0.2 degrees two theta and by the absence of peaks at about 8.2 and 16.0±0.2 degrees two theta. Preferably, "absence of peak" refers to an absence of a peak whose signal to noise ratio is higher than 2. The signal-to-noise ratio is computed by dividing the intensity of the peak by the amplitude of the baseline noise.

Alternatively, Crystalline form III can be characterized by XRD peaks at about 5.1, 7.7, 10.3, 14.8 and 22.0±0.2 degrees two theta and by the absence of peaks at about 7.2, 8.2, 15.5 and 16.0±0.2 degrees two theta; an X-ray powder diffraction pattern as depicted in FIG. 1; and combinations of this data. Crystalline form III may be further characterized by the X-ray powder diffraction pattern having peaks at 5.1, 7.7, 10.3, 14.8 and 22.0 degrees two theta ±0.2 degrees two theta and also having any one, any two, any three or more additional peaks selected from: 6.3, 9.7, 17.9, 20.6 and 23.4 two theta ±0.2 degrees two theta.

Crystalline Form III of Linaclotide may be characterized by a solid state $^{13}$C NMR having peaks at 18.5, 43.0, 49.9, 52.4, 56.5, 61.9, 115.7, 133.8, 169.1, 171.5±2 ppm or a solid state $^{13}$C NMR spectrum as depicted in FIG. 9.

Crystalline Form III of Linaclotide may be characterized by either a solid state $^{13}$C NMR having peaks at 18.5, 43.0, 49.9, 52.4, 56.5, 61.9, 115.7, 133.8, 169.1, 171.5±2 ppm, or a solid state $^{13}$C NMR spectrum as depicted in FIG. 9 in combination with the XRPD peaks according embodiment disclosed herein.

Crystalline Form III of Linaclotide may be characterized by each of the above characteristics alone and/or by all possible combinations.

The above crystalline Form III of Linaclotide may be obtained either as a wet form, or a dry form.

The crystalline Form III of Linaclotide according to any aspect or embodiment of the present invention may comprise: 10 wt % or less, 5 wt % or less, or 3 wt % or less of water.

The crystalline Form III of Linaclotide according to any aspect or embodiment of the present invention may comprise: 1.0 wt % or less, 0.5 wt % or less, or 0.3 wt % or less, of L-Asp Linaclotide impurity.

Crystalline Form III of Linaclotide according to any aspect or embodiment of the present invention may comprise: 1.0 wt % or less, 0.8 wt % or less, or 0.5 wt % or less, of Acetylated Linaclotide impurity.

Crystalline Form III of Linaclotide according to any aspect or embodiment of the present invention may comprise: 5 wt % or less, 3 wt % or less, or 2 wt % or less, of multimers. Crystalline Form III of Linaclotide according to any aspect or embodiment of the present invention may be chemically pure. In particular the crystalline form III of Linaclotide may have a chemical purity of: 90.0-100%, 95.0-100%, 98.0-100%, or 98.5-100%.

Crystalline Form III of Linaclotide according to any aspect or embodiment of the present invention may be polymorphically pure. In particular, the crystalline form III of Linaclotide may comprise: about 10% (w/w) or less, about 5% (w/w) or less, about 2% (w/w) or less, about 1% about 10 wt % or less, about 5% wt %, about 4 wt % or less, about 3 wt % or less, 2 wt % or less, about 1 wt % or less, about 0.5 wt % or less, or about 0.2 wt % or less of other solid state forms of Linaclotide.

The present invention encompasses a process for preparing crystalline Form III of Linaclotide as defined in any of the above aspects and embodiments. The process comprises solvent removal from a mixture comprising Linaclotide, ethanol and water. The Linaclotide Form III of the present invention may be obtained directly from the solvent removal process.

In one embodiment, the process comprises: (i) providing a mixture comprising Linaclotide, ethanol and water; (ii) distilling to remove solvents and other volatiles; and (iii) optionally adding ethanol (preferably absolute ethanol) and further distilling; and (iv) optionally repeating step (iii) one or more times. In this process, water is azeotropically removed from the mixture, preferably under reduced pressure. Other volatiles, if present, are typically also removed during the solvent stripping process. Preferably, the evaporation is carried out to remove most of the water and other volatiles, such that the water and volatiles content is reduced to an acceptable level (e.g. within ICH Guideline upper limits). The resulting crystalline form III of Linaclotide may be obtained directly from the solvent removal process. In particular, the resulting crystalline form III of Linaclotide may be obtained from the solvent removal process without further processing steps or without further isolation or crystallization steps. The mixture in (i) may be obtained by dissolving Linaclotide (e.g. Linaclotide containing volatiles) in ethanol and water. Alternatively the mixture in (i) may be prepared by adding ethanol, and optionally water, to an eluent obtained from HPLC purification of Linaclotide using a mobile phase comprising aqueous acetic acid and acetonitrile mobile phase, thereby forming a mixture comprising ethanol, water, acetonitrile and acetic acid.

Step (iii) may be repeated one or more times in order to further reduce the water content and/or acetonitrile content and/or acetic acid content of Linaclotide to a desired level, or to reduce the volatiles content of Linaclotide to a desired level.

The water content of the resulting Linaclotide after this treatment can be reduced to 10 wt % or less, 5 wt % or less, 3 wt % or less, 2 wt % or less or 1 wt % or less. The acetonitrile content of the resulting Linaclotide after this treatment can be reduced to: 410 ppm or less, 350 ppm or less 250 ppm or less, 100 ppm, 75 ppm or less, or 50 ppm or less.

The distilling can be carried out under reduced pressure, and is preferably carried out at a temperature: not more than 60° C., not more than 55° C. or not more than 45° C. Preferably the distilling can be carried out at a temperature of between: about 20 to about 60° C., about 25 to about 55° C., or about 30 to about 45° C.

Preferably, in step (i), the ethanol and water in the mixture in step (i) are in a ratio of about 90:10 to about 98:2 v/v, preferably about 92:8 to about 97:3 and more preferably about 95:5 v/v.

The process may further comprise processing the Linaclotide form III with at least one pharmaceutically acceptable excipient to form a pharmaceutical composition or a pharmaceutical dosage form.

The present invention further encompasses crystalline form III of Linaclotide obtainable by the above-described process.

The present invention further relates to the use of a crystalline form III of Linaclotide as defined herein for the preparation of: other solid state forms of Linaclotide or other salts of Linaclotide and their solid state forms, or for the preparation of a composition comprising: Form III of Linaclotide, another solid state form of Linaclotide or a salt of Linaclotide or solid state forms of a salt of Linaclotide. The present invention also relates to the use of a crystalline form III of Linaclotide as defined herein, for the preparation of amorphous form of Linaclotide, or for the preparation of a composition comprising amorphous form of Linaclotide, or for the preparation of a composition comprising amorphous form and Form III of Linaclotide, preferably for the preparation of a composition comprising amorphous form of Linaclotide.

In a further aspect of the present invention, there is provided the use of a crystalline form III of Linaclotide as defined herein for the preparation of a pharmaceutical composition or dosage form. The pharmaceutical dosage form may comprise Linaclotide in any solid state form. For example, the pharmaceutical dosage form may comprise amorphous form of Linaclotide which may be formed by spraying a Linaclotide or a solution of Linaclotide onto a pharmaceutically acceptable carrier or inert core.

In a further aspect, the present invention provides a process for removing water from Linaclotide comprising evaporation of a solution of Linaclotide comprising an azeotropic mixture of an organic solvent and water, preferably wherein the process comprises evaporation the solution to dryness, thereby forming Linaclotide crystalline form III as defined herein. The organic solvent may preferably be acetonitrile and/or ethanol, and more preferably the organic solvent is ethanol.

The present inventors have found that the use of ethanol is particularly advantageous. Surprisingly, it has been found that ethanol is an effective stabilizing agent for aqueous Linaclotide solutions. Particularly, ethanol was able to retard the formation of multimers derived from Linaclotide in such solutions. Accordingly, a further aspect of the present invention provides the use of ethanol as a stabilizing agent (particularly for the retardation of multimer formation) in aqueous Linaclotide solutions. Preferably, the aqueous Linaclotide solution comprises water and a water-miscible organic solvent (particularly a non-hydroxylic solvent, and preferably acetonitrile), and optionally a water-soluble organic acid (preferably acetic acid).

In a further aspect of the present invention, there is provided a process for the purification of Linaclotide by a two-step HPLC process, wherein the elution is conducted under different pH conditions. In particular, the process comprises subjecting Linaclotide (such a crude Linaclotide from a sequential synthesis and cyclization) to: (A) column chromatography of the crude Linaclotide on reversed phase column, preferably a silica gel column, wherein the mobile phase comprises a gradient of an aqueous buffer and acetonitrile, and optionally repeating, and (B) column chromatography on a reversed phase column, preferably a silica gel column, wherein the mobile phase comprises a gradient of aqueous acetic acid and acetonitrile and optionally repeating. Step (A) may be repeated a number of times in order to further purify the Linaclotide to a higher purity. Step (B) may also be repeated a number of times in order to further purity the Linaclotide to a higher purity. After step (B), a further step, step (C), may be carried out, whereby the Linaclotide is further eluted from the column with a mobile phase comprising aqueous acetic acid and at least one of acetonitrile or ethanol, wherein the mobile phase comprises at least 50% acetonitrile or at least 50% ethanol, or at least 50% of a mixture of acetonitrile and ethanol. The reversed phase column can be any suitable column, e.g. a silica gel column, and preferably is a C18 column.

Preferably, in step (B), the water-soluble organic acid is acetic acid.

Preferably, the aqueous buffer in (A) has a pH of about: 6.5 to about 8.5, about 6.7.1 to about 8.0, or about 7.0 to about 7.5. In step (A), the ratio of acetonitrile to the aqueous buffer (vol:vol) in (A) is preferably from: about 2:98 to about 50:50, or from about 4:96 to about 40:60, or about 5:95 to about 30:70. The gradient elution in step (A) may comprise from about 5:95 (vol acetonitrile:vol aqueous buffer) to about 60:40 (vol acetonitrile:vol aqueous buffer), or from about 5:95 (vol acetonitrile:vol aqueous buffer) to about 50:50 (vol acetonitrile:vol aqueous buffer), or from about 5:95 (vol acetonitrile:vol aqueous buffer) to about 40:60 (vol acetonitrile:vol aqueous buffer). Preferably, the aqueous buffer in step (A) is a phosphate buffer, preferably in a concentration of: about 0.001 M to about 0.5 M, about 0.005 M to about 0.1 M, about 0.008 M to about 0.025 M, or about 0.008 M to about 0.015 M.

Prior to step (B), the pH of the Linaclotide solution from step (A) is adjusted to an acidic pH, preferably a pH of about 1.5 to about 5.0, about 1.8 to about 4.0, about 1.8 to about 3.0, about 1.8 to about 2.8, or about 2.0 to about 2.5, preferably wherein the pH is adjusted using phosphoric acid.

Preferably, the aqueous acetic acid in step (B) comprises water and acetic acid, wherein the acetic acid is in an amount of: about 0.01 to about 5%, about 0.1 to about 2.5% v/v, about 0.1 to about 1.0% v/v, about 0.1 to about 0.5% v/v, or about 0.1 to about 0.25% v/v, or about 0.2% vol/vol. In preferred embodiments, the ratio of acetonitrile to the aqueous acetic acid (vol:vol) is from: about 2:98 to about 50:50, or from about 4:96 to about 40:60, or about 5:95 to about 30:70. The gradient elution in step (B) may comprise from: about 5:95 (vol acetonitrile:vol aqueous acetic acid) to about 95:5 (vol acetonitrile:vol aqueous acetic acid), or from about 20:80 (vol acetonitrile:vol aqueous acetic acid) to about 60:40 (vol acetonitrile:vol aqueous acetic acid).

The process may be conducted such that step (A) is repeated number of times in order to obtain a purity of: about 80% to about 98%, about 85% to about 98%, or about 87% to about 98%, by HPLC. Step (B) may be repeated to obtain a purity of: about 95% to about 100%, about 96% to about 99.8%, about 97% to about 99.5%, or about 98% to about 99.5%, by HPLC.

Preferably, the above process comprises further eluting Linaclotide from the column with a mobile phase comprising aqueous acetic acid and one or both of acetonitrile and/or ethanol, wherein the mobile phase comprises aqueous acetic acid and: at least 50% acetonitrile, or at least 50% ethanol or at least 50% of a mixture of acetonitrile and ethanol, in accordance with step (C). Preferably, the aqueous acid component of the mobile phase in (C) comprises water and acetic acid, wherein the acetic acid is in an amount of: about 0.01% to about 2.0%, about 0.1% to about 1.0%, about 0.1% to about 0.5%, about 0.15% to about 0.25%, or about 0.2% vol/vol relative to water. The mobile phase in step (C) may comprise aqueous acetic acid and acetonitrile, wherein the acetonitrile in the mobile phase is in an amount of: about 50% to about 95%, about 60% to about 90%, about 65% to about 85%, about 65% to about 75%, or about 70% vol/vol. More preferably, the mobile phase in step (C) can be aqueous acetic acid and acetonitrile, wherein the aqueous acetic acid comprises water and acetic acid, wherein the acetic acid is in an amount of: about 0.01% to about 0.5%, about 0.15% to about 0.25%, or about 0.2% vol/vol relative to water, and wherein the acetonitrile in the mobile phase can be present in an amount of about 60% to about 75%, or about 70% vol/vol. The mobile phase in step (C) may alternatively comprise aqueous acetic acid and ethanol, preferably wherein the ethanol is present in the mobile phase in an amount of: about 50% to about 95%, about 70% to about 95%, about 80% to about 95%, about 85% to about 95%, or about 90% vol/vol. Preferably the mobile phase in step (C) may be aqueous acetic acid and ethanol, wherein the aqueous acetic acid may comprise water and acetic acid, wherein the acetic acid is in an amount of: about 0.01% to about 0.5%, about 0.15% to about 0.25%, or about 0.2% vol/vol relative to water, and wherein the ethanol in the mobile phase is in an amount of about 50% to about 95%, or about 90% vol/vol. As a further alternative, the mobile phase in step (C) may comprise aqueous acetic acid, and a mixture of ethanol with acetonitrile, preferably wherein the mixture of ethanol and acetonitrile in the mobile phase is in an amount of: about 50% to about 95%, about 60% to about 95%, about 70% to about 95%, about 88% to about 95%, or about 90% vol/vol. Preferably, the mobile phase in step (C) can be aqueous acetic acid and a mixture of ethanol with acetonitrile, wherein the aqueous acetic acid comprises water and acetic acid, wherein the acetic acid is in an amount of: about 0.01% to about 0.5%, about 0.15% to about 0.25%, or about 0.2% vol/vol relative to water, and wherein the mixture of ethanol and acetonitrile in the mobile phase is in an amount of about 50% to about 95%, about 80 to about 90%, or about 85 to about 90% vol/vol.

Linaclotide obtained after step (B) or step (C) preferably contains: 1.0 wt % or less, 0.5 wt % or less, or 0.3 wt % or less, of L-Asp Linaclotide impurity as defined above. The Linaclotide obtained after step (B) or step (C) may comprise: 1.0 wt % or less, 0.8 wt % or less, or 0.5 wt % or less, of Acetylated Linaclotide impurity as defined above. The Linaclotide obtained after step (B) or step (C) may comprise: 5 wt % or less, 3 wt % or less, or 2 wt % or less, of multimers as defined above.

The above HPLC purification process enables the direct production of Linaclotide [i.e. after step (B) after or step (C)], preferably after step (C)), wherein the Linaclotide can have a purity of: 98.5% or more, 99.0% or more, 99.5% or more, 99.8% or more, 99.9% or more, 99.95% or more.

The Linaclotide obtained from the above HPLC purification process may be further treated in order to reduce water and other volatiles. Thus, the eluted fraction containing Linaclotide from step (B) or step (C), preferably step (C), can be subjected to a process comprising: (a) adding ethanol, (b) distilling to remove solvents and other volatiles, (c) adding ethanol (preferably absolute ethanol), (d) distilling to remove solvents and other volatiles, and (e) optionally repeating steps (c) and (d).

Step (b) is preferably carried out at a temperature of: not more than about 60° C., not more than about 55° C., not more than about 50° C., not more than about 45° C., or not more than about 35° C., preferably under reduced pressure. Step (b) may be carried out at a temperature of: about 20 to about 60° C., about 30 to about 55° C., or about 35 to about 50° C., or about 35 to about 5° C. Step (d) is preferably carried out at a temperature of: not more than not more than about 60° C., not more than about 55° C., not more than about 50° C., not more than about 45° C., or not more than about 35° C., preferably under reduced pressure. Alternatively, step (d) may be carried out at a temperature between: about 20 to about 60° C., about 25 to about 55° C., about 25° C. to about 45° C., or about 25° C. to about 35° C., preferably under reduced pressure. Preferably, step (b) and/or step (d), and preferably both steps (b) and (d), are carried out under reduced pressure.

Preferably, ethanol in step (a) is added to form a mixture wherein the ethanol-water ratio in the mixture is: about 90:10 to about 98:2, preferably about 92:8 to about 97:3 and more preferably about 95:5 vol/vol.

Additional removal of water and/or other volatiles can be achieved by repeating steps (c) and (d) at least once, or at least twice, or at least three times, to obtain Linaclotide having reduced water and/or other volatiles content.

Advantageously, the Linaclotide may be obtained directly after step (d) or after step (e). Thus, purified Linaclotide may be obtained without further treatment following the stripping process using ethanol as described above. The purified Linaclotide may have a purity of 98.5% or more, 99.0% or more, 99.5% or more, 99.8% or more, 99.9% or more, 99.95% or more. Moreover, the above process enables the production of Linaclotide having a water content of: 10 wt % or less, 7 wt % or less, 5 wt % or less, 3 wt % or less, or 2 wt % or less. In the case where the solution of Linaclotide comprising ethanol and water is obtained as a eluent from a HPLC purification process using acetonitrile/aqueous acetic acid mobile phase, the above process can also reduce the acetonitrile content in the final Linaclotide product to: 410 ppm or less, 350 ppm or less 250 ppm or less, 100 ppm, 75 ppm or less, or 50 ppm or less.

Preferably, the Linaclotide obtained from the above-described process is crystalline Form III as described herein. The purified Linaclotide can be further processed with at least one pharmaceutically acceptable excipient to form a pharmaceutical composition or a dosage form. The pharmaceutical composition or dosage form can comprise Linaclotide in any solid state form, for example, the pharmaceutical composition or dosage form may comprise Linaclotide in amorphous form (for example, wherein Linaclotide is sprayed—e.g. as a solution—onto a pharmaceutically acceptable excipient or an inert core).

The present invention further comprises a composition, preferably a pharmaceutical composition or a dosage form, comprising a mixture of Form III of Linaclotide as defined herein with amorphous Linaclotide. The composition further comprises at least one pharmaceutically acceptable excipient.

In a further aspect, the crystalline Linaclotide as defined in any aspect or embodiment of the present invention can be used for the manufacture of a pharmaceutical composition. The pharmaceutical composition may contain Linaclotide in any solid state form (e.g. amorphous form).

The above described solid state form III can be used to prepare other solid state forms of Linaclotide; particularly amorphous form or other salts of Linaclotide and their solid state forms.

The above described solid state form III of Linaclotide can be used to prepare pharmaceutical compositions and formulations. In certain embodiments, the present invention comprises the above described solid state forms of Linaclotide for use in the preparation of pharmaceutical compositions and formulations.

The present invention comprises pharmaceutical compositions and formulations comprising Linaclotide form III.

The pharmaceutical formulations can be prepared by a process comprising combining a solid state form of Linaclotide form III with at least one pharmaceutically acceptable excipient.

The above solid state form of Linaclotide III can also be used as a medicament, particularly for the treatment of gastrointestinal disorders.

The present invention further encompasses 1) the use of Linaclotide form III in the manufacture of a pharmaceutical composition, and 2) a method of treating a subject suffering from gastrointestinal disorders, or otherwise in need of the treatment, comprising administration of an effective amount of a pharmaceutical composition comprising the above crystalline form III to a person in need of the treatment.

The present invention comprises pharmaceutical compositions and formulations comprising Linaclotide form III.

The pharmaceutical formulations can be prepared by a process comprising combining Linaclotide form III with at least one pharmaceutically acceptable excipient.

The above Linaclotide form III can also be used as a medicament, particularly for the treatment of gastrointestinal disorders.

The present invention further encompasses 1) the use of the above-described Linaclotide form III in the manufacture of a pharmaceutical composition, and 2) a method of treating a subject suffering from gastrointestinal disorders, or otherwise in need of the treatment, comprising administration of an effective amount of a pharmaceutical composition comprising Linaclotide form III described herein to a person in need of the treatment.

Another aspect of the present invention provides crystalline Linaclotide, designated form IV, characterized by data selected from one or more of the following: X-ray powder diffraction pattern having peaks at 5.3, 7.1, 10.8, 15.1, and 17.6 degrees two theta ±0.2 degrees two theta; an X-ray powder diffraction pattern as depicted in FIG. 2; and combinations of this data.

Crystalline form IV of Linaclotide can be further characterized by the X-ray powder diffraction pattern having peaks at 5.3, 7.1, 10.8, 15.1, and 17.6 degrees two theta ±0.2 degrees two theta and also having any one, any two, any three or more additional peaks selected from: 6.5, 19.4, 21.3, 22.8 and 25.8 two theta ±0.2 degrees two theta.

Crystalline Form IV of Linaclotide may be characterized by each of the above characteristics alone and/or by all possible combinations.

In one embodiment, the present invention comprises crystalline Linaclotide, designated form V, characterized by data selected from one or more of the following: X-ray powder diffraction pattern having peaks at 7.7, 10.6, 8.9, 10.0, and 11.9 degrees two theta ±0.2 degrees two theta; an X-ray powder diffraction pattern as depicted in FIG. 3; and combinations of this data.

Crystalline form V of Linaclotide can be further characterized by the X-ray powder diffraction pattern having peaks at 7.7, 10.6, 8.9, 10.0, and 11.9 degrees two theta ±0.2 degrees two theta and also having any one, any two, any three or more additional peaks selected from: 14.4, 15.1, 19.4, 21.3 and 23.3 two theta ±0.2 degrees two theta.

Crystalline Form V of Linaclotide may be characterized by each of the above characteristics alone and/or by all possible combinations.

In one embodiment, the present invention comprises crystalline Linaclotide, designated form VI, characterized by data selected from one or more of the following: X-ray powder diffraction pattern having peaks at 5.4, 7.9, 10.7, 17.5 and 20.2 degrees two theta ±0.2 degrees two theta; an X-ray powder diffraction pattern as depicted in FIG. 4; and combinations of this data.

Crystalline form VI of Linaclotide can be further characterized by the X-ray powder diffraction pattern having peaks at 5.4, 7.9, 10.7, 17.5 and 20.2 degrees two theta ±0.2 degrees two theta and also having any one, any two, any three or more additional peaks selected from: 6.5, 12.4, 13.8, 20.8 and 22.9 two theta ±0.2 degrees two theta.

Crystalline Form VI of Linaclotide may be characterized by each of the above characteristics alone and/or by all possible combinations.

In one embodiment, the present invention comprises crystalline Linaclotide, designated form VII, characterized by data selected from one or more of the following: X-ray powder diffraction pattern having peaks at 5.4, 8.9, 12.0, 14.4 and 21.4 degrees two theta ±0.2 degrees two theta; an X-ray powder diffraction pattern as depicted in FIG. 5; and combinations of this data.

Crystalline form VII of Linaclotide can be further characterized by the X-ray powder diffraction pattern having peaks at 5.4, 8.9, 12.0, 14.4 and 21.4 degrees two theta ±0.2 degrees two theta and also having any one, any two, any three or more additional peaks selected from: 6.4, 10.6, 19.5, 23.4, and 27.8 two theta ±0.2 degrees two theta and by the absence of peaks at about 8.2 and 16.0±0.2 degrees two theta.

Crystalline Form VII of Linaclotide may be characterized by each of the above characteristics alone and/or by all possible combinations.

The above crystalline Forms IV, V, VI and VII of Linaclotide may be obtained either as wet forms, or dry forms.

The above described solid state forms IV, V, VI and VII can be used to prepare other solid state forms of Linaclotide; particularly amorphous form or other salts of Linaclotide and their solid state forms.

The above described solid state forms IV, V, VI and VII of Linaclotide can be used to prepare pharmaceutical compositions and formulations. In certain embodiments, the present invention comprises the above described solid state forms of Linaclotide for use in the preparation of pharmaceutical compositions and formulations.

The present invention comprises pharmaceutical compositions and formulations comprising Linaclotide forms IV, V, VI or VII of the present invention.

The pharmaceutical formulations can be prepared by a process comprising combining a solid state form of Linaclotide forms IV, V, VI or VII of the present invention with at least one pharmaceutically acceptable excipient.

The above solid state forms of Linaclotide forms IV, V, VI or VII of the present invention can also be used as a medicament, particularly for the treatment of gastrointestinal disorders.

The present invention further encompasses 1) the use of the above-described solid state Linaclotide forms IV, V, VI or VII in the manufacture of a pharmaceutical composition, and 2) a method of treating a subject suffering from gastrointestinal disorders, or otherwise in need of the treatment, comprising administration of an effective amount of a pharmaceutical composition comprising the above crystalline forms IV, V, VI or VII of Linaclotide described herein to a person in need of the treatment.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

X-Ray Powder Diffraction method:

After sample being gently ground in a mortar and pestle it was applied directly on a silicon plate holder. The analyses were performed on ARL (SCINTAG) powder X-Ray diffractometer model XTRA equipped with a solid state detector. Copper radiation of 1.5418 Å was used. Scanning parameters: range: 2-40 degrees two-theta; scan mode: continuous scan; step size: 0.05°, and at a rate of 3 deg/min. The described peak positions were determined using silicon powder as an internal standard in an admixture with the sample measured. Due to number rounding the position of a few peaks was corrected based on the Si position.

Optical Microscope Analysis:

Microscopic analysis of the samples was carried out using Light microscope Leica DM2500P. All samples were suspended in light mineral oil, and dispersed on a glass slide.

SS-NMR Analysis

Solid state $^{13}$C NMR was carried out at 125 MHz using Bruker Avance II+500, with an SB probe using 4 mm rotors. Magic angle was set using KBr. The homogeneity of magnetic field was checked using adamantine. Parameters for Cross polarization were optimized using glycine. Spectral reference was set according to glycine as external standard (176.03 ppm for low field carboxyl signal). The following scanning parameters were employed:
Pulse program: variable amplitude cross polarization with high power decoupling
Magic Angle Spinning Rate: 11 kHz
Delay time: 2 sec.
Contact time: 2 ms
Number of Scans: 2048 scans (form III), 32768 scans (amorphous).

EXAMPLES

Reference Example

The Linaclotide can be prepared by using standard linear (sequential) syntheses using an automated solid-phase peptide synthesizer as described in U.S. Pat. No. 7,371,727 and WO2014/188011, followed by cyclization as described in Biopolymers (Peptide Science) 96(1): 69-80, 2011 (Miriam Góngora-Benitez, Judit Tulla-Puche, Marta Paradis-Bas, Oleg Werbitzky, Matthieu Giraud, Fernando Albericio), 2010 Wiley Periodicals, Inc.

Example 1: Preparation of Crystalline Linaclotide Form III

Linaclotide was purified with preparative HPLC using a gradient of Acetic acid solution (0.2% AcOH solution) and acetonitrile. In the last step, the Linaclotide API was eluted from the preparative column with 30% aq. solution (0.05% AcOH in water) and 70% Acetonitrile. The solution (16 liter) was then diluted with absolute Ethanol (152 liter) to form a solution with water/Ethanol ratio 5/95. The obtained solution was evaporated until dryness (the bath temperature was set to 40±5° C.). Ethanol was added to the obtained solid (using 10% of the flask volume (2 liter)), and further evaporated to dryness (bath temperature was set to 30±5° C.). This step was repeated three times. The product was analyzed by PXRD, the PXRD pattern is shown in FIG. 1.

Example 2: Preparation of Crystalline Linaclotide Form IV

A sample of approximately 100 mg of Linaclotide Form III was gently ground in a mortar and pestle, with approximately 2 ml of IPA. The resulting material was tested by XRD, and found to be Form IV. The product was analyzed by PXRD, the PXRD pattern is shown in FIG. 2.

Example 3: Preparation of Crystalline Linaclotide Form V

A sample of approximately 100 mg of Linaclotide Form III was gently ground in a mortar and pestle, with approximately 2 ml of H$_2$O. The resulting material was tested by XRD, and found to be Form V. The product was analyzed by PXRD, the PXRD pattern is shown in FIG. 3.

Example 4: Preparation of Crystalline Linaclotide Form VI

A sample of approximately 100 mg of Linaclotide Form III was exposed to 0% RH @ RT for 7D (7 days). The resulting material was tested by XRD, and found to be Form VI. The product was analyzed by PXRD, the PXRD pattern is shown in FIG. 4.

Example 5A: Preparation of Crystalline Linaclotide Form VII

A sample of approximately 100 mg of Linaclotide Form III was exposed to 80% RH @ RT for 7D (7 days). The resulting material was tested by XRD, and found to be Form VII. The product was analyzed by PXRD, the PXRD pattern is shown in FIG. 5.

Example 5B: Preparation of Crystalline Linaclotide Form VII

A sample of approximately 100 mg of Linaclotide Form III was exposed to 100° C. for 30 min. The resulting material was tested by XRD, and found to be Form VII.

Example 6: Preparation of Linaclotide Form III

Crude Linaclotide (842 gram) (71.3% purity) after cyclization was purified with preparative HPLC on C18 RP column using 0.01M phosphate buffer (pH 7.2) and acetonitrile (increased acetonitrile from 5% to 30% v/v over the run according to gradient program). After 7 purification cycles 516 gram (61% yield) of the Linaclotide reached 94.3% purity. The pH of the solution containing 516 gram Linaclotide obtained from the previous stage was adjusted to 2.0-2.5 using phosphoric acid. Additional 8 purification cycles on C18 RP column using water with 0.2% AcOH and acetonitrile (pH of about 3) (increased acetonitrile from 5% to 30% v/v over the run according to gradient program) yielded 470 gram (91% yield) Linaclotide having 98.80% purity. In the last step, the Linaclotide (API) was eluted from the preparative HPLC column with 30% aq. solution (0.2% AcOH in water) and 70% Acetonitrile*. The solution (16 liter, 235 gram, 98.8% purity) was then diluted with absolute Ethanol (152 litres) to form a solution with water/Ethanol ratio of 5/95. The obtained solution was evaporated until dryness (the bath temperature was set to 40±5° C.) under reduced pressure. Ethanol was added to the obtained solid (using 10% of the flask volume (2 liter)), and further evaporated to dryness (bath temperature was set to 30±5° C.), This step was repeated three times. The product was analyzed by PXRD, and the PXRD pattern is shown in FIG. 1.

* The Linaclotide API may also be eluted from the preparative HPLC column with a 10% aqueous solution (0.2% AcOH in water) and 90% ethanol, or with a 10% aqueous solution (0.2% AcOH in water) and 90% of a mixture of ethanol/acetonitrile.

Example 7: Stabilizing Linaclotide Solutions

Solutions of Linaclotide in: (A): a 1:1 mixture of 0.2% AcOH: ACN or (B): a 1:1:9.5 mixture of 0.2% AcOH:ACN: EtOH, were stored for 12 days at room temperature (RT) in sealed vials. The solutions were analysed by (HPLC-size exclusion chromatography) (HPLC-SEC), for % multimers (the major degradants present) content (see table below):

|  | % Multimers according to HPLC-SEC method | |
|---|---|---|
| Day | (A) Without EtOH | (B) with EtOH |
| 0 | 1.72 | 1.54 |
| 1 | 1.87 | 1.66 |
| 2 | 1.70 | 2.17 |
| 5 | 3.05 | 2.34 |
| 6 | 3.75 | 3.22 |
| 7 | 3.83 | 3.54 |
| 8 | 4.61 | 3.64 |
| 11 | 6.47 | 3.62 |
| 12 | 7.18 | 4.88 |

The results are graphically represented in FIG. 6. From these results, it can be seen that ethanol surprisingly has a stabilizing effect on the Linaclotide solution, reducing the formation of multimers during storage.

Example 8: Particle Morphology of Form III Linaclotide

Figure 7B:
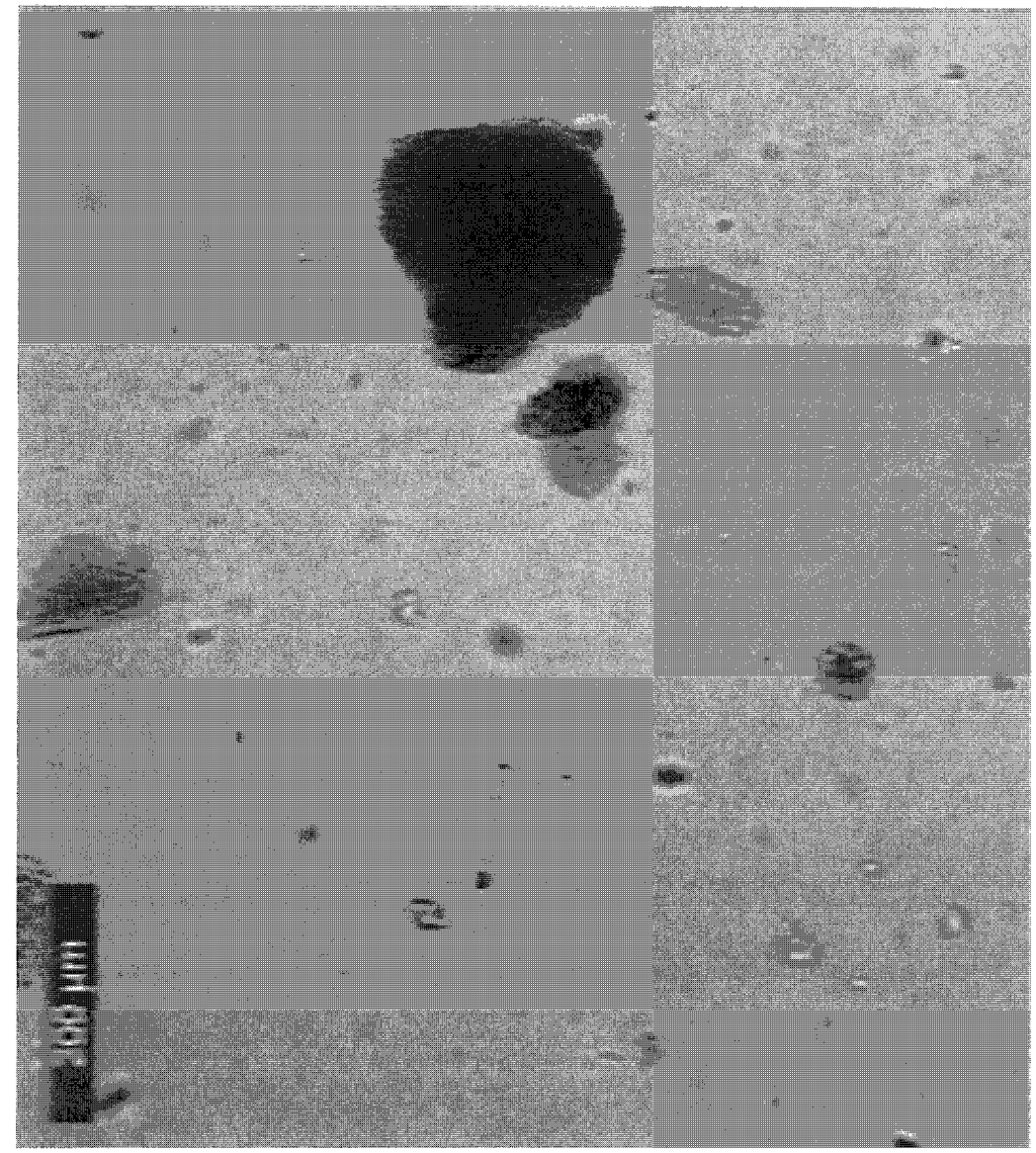
Figure 8A:
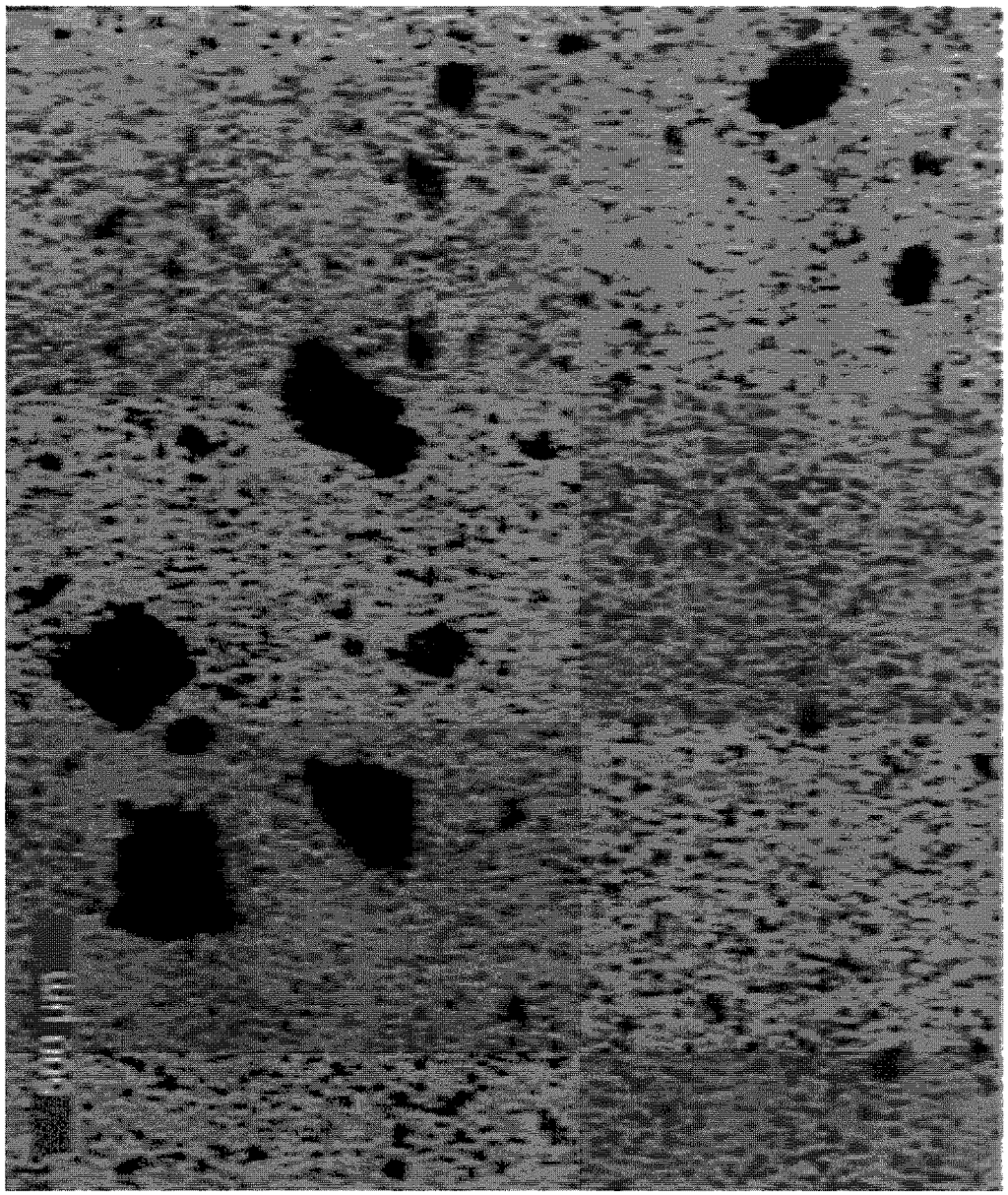
FIGS. 8A and 8B show microscope images of amorphous Linaclotide
Figure 8B:
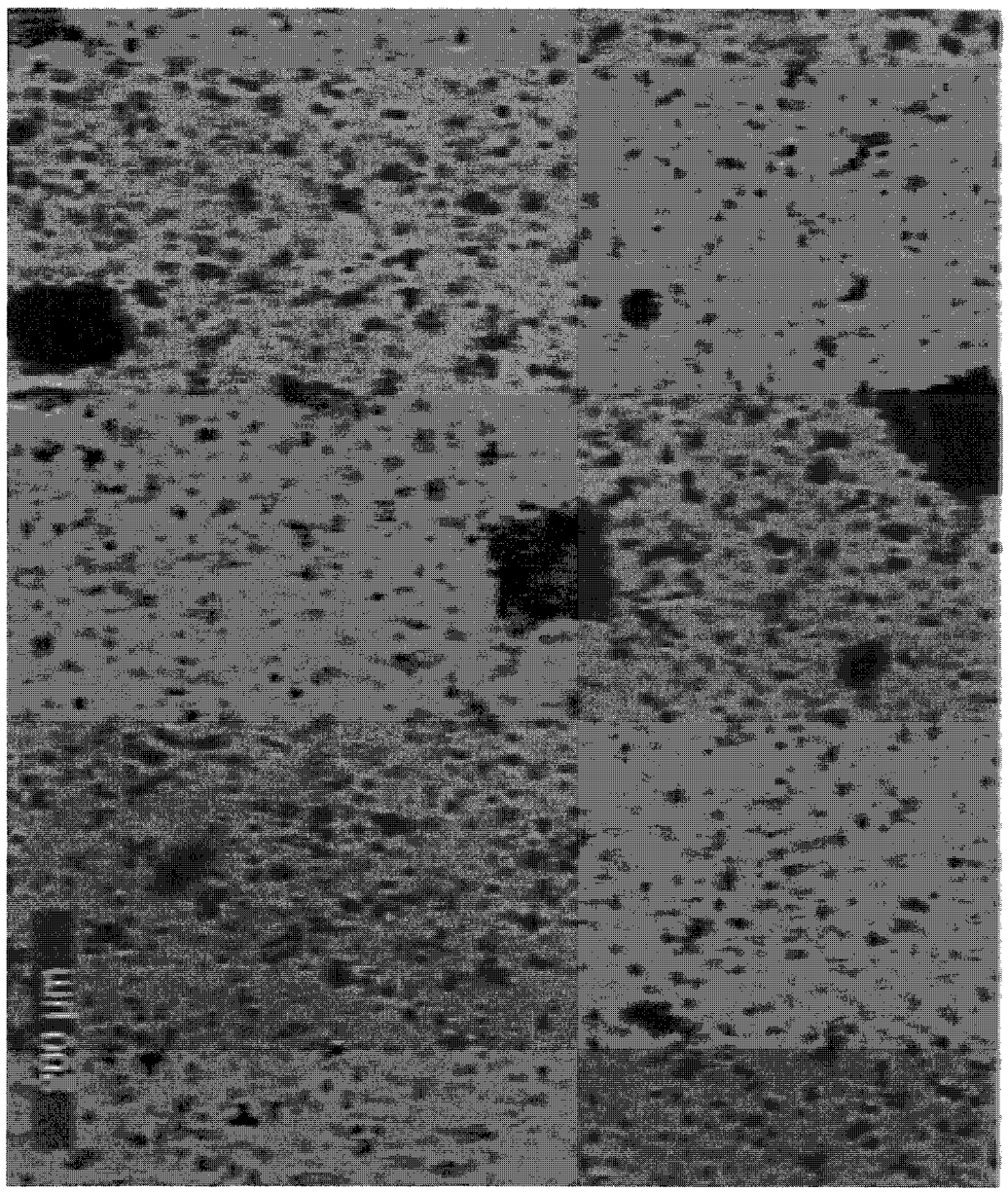

Optical microscope photographs show that the Form III Linaclotide comprises primarily larger irregular plate-shaped particles (FIGS. 7a and 7b), as opposed to the amorphous form, which comprises primarily small spherical particles (FIGS. 8a and 8b).

Small spherical particles have a tendency to block filters, and are less stable due to their greater surface area. Additionally, due to the high levels of aeration within the bulk content, small spherical particles tend to exhibit poorer flow properties. These represent significant disadvantages for filtration, drying, storage, and processing steps. In contrast, the crystalline form of the present invention is stable, does not show a tendency to block filters, and does not suffer from poor flowability.

Example 9: Solid State $^{13}$C NMR of Linaclotide Form III

The solid state $^{13}$C NMR of Linaclotide Form III is shown in FIG. 9. The main peaks are at: 18.5, 43.0, 49.9, 52.4, 56.5, 61.9, 115.7, 133.8, 169.1, 171.5±2 ppm.

The solid state $^{13}$C NMR of Amorphous Linaclotide is shown in FIG. 10. The spectrum shows broad peaks in the area of about 53 and 173 ppm.

Example 10: Stability of Linaclotide Form III

Linaclotide Form III according to the present invention was subjected to a stability test in accordance with U.S. Pat. No. 8,222,201, Example 3 (storage in sealed 45 cc. high density polyethylene bottles at 40° C. and 75% relative humidity). As disclosed in Example 3, Table 13 of U.S. Pat. No. 8,222,201, crystalline Form alpha was found to contain 5.7 wt % of hydrolysis product (i.e., L-Asp Linaclotide impurity) following the storage for 3 months under these conditions. Surprisingly, after 4 weeks, the crystalline Form III Linaclotide sample contained only 0.22% of the Linaclotide hydrolysis product, extrapolated to 0.45 wt % after 3 months. Accordingly, the crystalline Form III of the present invention is surprisingly more stable.

Further aspects and embodiments of the present invention can be found in the following numbered paragraphs:

1. Crystalline Linaclotide, designated form IV, characterized by data selected from one or more of the following: X-ray powder diffraction pattern having peaks at 5.3, 7.1, 10.8, 15.1, and 17.6 degrees two theta ±0.2 degrees two theta; or an X-ray powder diffraction pattern as depicted in FIG. 2; or combinations of this data.

2. Crystalline form IV of Linaclotide according to Paragraph 1, which is characterized by an X-ray powder diffraction pattern having peaks at 5.3, 7.1, 10.8, 15.1, and 17.6 degrees two theta ±0.2 degrees two theta and also having any one, any two, any three or more additional peaks selected from: 6.5, 19.4, 21.3, 22.8 and 25.8 two theta ±0.2 degrees two theta.

3. Crystalline Linaclotide, designated form V, characterized by data selected from one or more of the following: X-ray powder diffraction pattern having peaks at 7.7, 10.6, 8.9, 10.0, and 11.9 degrees two theta ±0.2 degrees two theta; or an X-ray powder diffraction pattern as depicted in FIG. 3; or combinations of this data.

4. Crystalline form V of Linaclotide according to Paragraph 3, which is characterized by an X-ray powder diffraction pattern having peaks at 7.7, 10.6, 8.9, 10.0, and 11.9 degrees two theta ±0.2 degrees two theta and also having any one, any two, any three or more additional peaks selected from: 14.4, 15.1, 19.4, 21.3 and 23.3 two theta ±0.2 degrees two theta.

5. Crystalline Linaclotide, designated form VI, characterized by data selected from one or more of the following: X-ray powder diffraction pattern having peaks at 5.4, 7.9, 10.7, 17.5 and 20.2 degrees two theta ±0.2 degrees two theta; or an X-ray powder diffraction pattern as depicted in FIG. 4; or combinations of this data.

6. Crystalline form VI of Linaclotide according to Paragraph 5, characterized by an X-ray powder diffraction pattern having peaks at 5.4, 7.9, 10.7, 17.5 and 20.2 degrees two theta ±0.2 degrees two theta and also having any one, any two, any three or more additional peaks selected from: 6.5, 12.4, 13.8, 20.8 and 22.9 two theta ±0.2 degrees two theta.

7. Crystalline Linaclotide, designated form VII, characterized by data selected from one or more of the following: X-ray powder diffraction pattern having peaks at 5.4, 8.9, 12.0, 14.4 and 21.4 degrees two theta ±0.2 degrees two theta; or an X-ray powder diffraction pattern as depicted in FIG. 5; or combinations of this data.
8. Crystalline form VII of Linaclotide according to Paragraph 7, characterized by the X-ray powder diffraction pattern having peaks at 5.4, 8.9, 12.0, 14.4 and 21.4 degrees two theta ±0.2 degrees two theta and also having any one, any two, any three or more additional peaks selected from: 6.4, 10.6, 19.5, 23.4, and 27.8 two theta ±0.2 degrees two theta and by the absence of peaks at about 8.2 and 16.0±0.2 degrees two theta.
9. A crystalline form of Linaclotide according to any of Paragraphs 1-8, comprising: 10 wt % or less, 5 wt % or less, or 3 wt % or less of water.
10. A crystalline form of Linaclotide according to any of Paragraphs 1-9, comprising: 1.0 wt % or less, 0.5 wt % or less, or 0.3 wt % or less, of L-Asp Linaclotide impurity.
11. A crystalline form of Linaclotide according to any of Paragraphs 1-10, comprising: 1.0 wt % or less, 0.8 wt % or less, or 0.5 wt % or less, of Acetylated Linaclotide impurity.
12. A crystalline form of Linaclotide according to any of Paragraphs 1-11, comprising: 5 wt % or less, 3 wt % or less, or 2 wt % or less, of multimers.
13. A crystalline form of Linaclotide according to any of Paragraphs 1-12, having a chemical purity of: 90.0-100%, 95.0-100%, 98.0-100%, or 98.5-100%.
14. A crystalline form of Linaclotide according to any of Paragraphs 1-13, comprising: about 10% (w/w) or less, about 5% (w/w) or less, about 2% (w/w) or less, about 1% about 10 wt % or less, about 5% wt %, about 4 wt % or less, about 3 wt % or less, 2 wt % or less, about 1 wt % or less, about 0.5 wt % or less, or about 0.2 wt % or less of other solid state forms of Linaclotide.
15. Use of a crystalline form of Linaclotide according to any of Paragraphs 1-14 for preparing other solid state forms of Linaclotide; particularly amorphous form or other salts of Linaclotide and their solid state forms.
16. Use of a crystalline form of Linaclotide according to any of Paragraphs 1-14 for preparing pharmaceutical compositions and formulations.
17. A crystalline form according to any of Paragraphs 1-14 for use in the preparation of pharmaceutical compositions and formulations.
18. A pharmaceutical composition comprising a crystalline form of Linaclotide according to any of Paragraphs 1-14 and at least one pharmaceutically acceptable excipient.
19. A process for preparing a composition according to Paragraph 18, comprising combining a solid state form of Linaclotide as defined in any of Paragraphs 1-14 with at least one pharmaceutically acceptable excipient.
20. A process for preparing a composition according to Paragraph 18, comprising processing a solid state form of Linaclotide as defined in any of Paragraphs 1-14 with at least one pharmaceutically acceptable excipient to form a pharmaceutical composition or formulation.
21. A crystalline form of Linaclotide as defined in any of Paragraphs 1-14 for use as a medicament, particularly for the treatment of gastrointestinal disorders.
22. A method of treating a subject suffering from gastrointestinal disorders, or otherwise in need of the treatment, comprising administration of an effective amount of a pharmaceutical composition comprising a crystalline form of Linaclotide as defined in any of Paragraphs 1-14 to a person in need of the treatment.

The invention claimed is:

1. Crystalline Form III of Linaclotide characterized by an X-ray powder diffraction pattern having peaks at 5.1, 7.7, 10.3, 14.8 and 22.0 degrees two theta ±0.2 degrees two theta; and optionally further characterized by data selected from one or more of the following:
   (i) an X-ray powder diffraction pattern as depicted in FIG. 1; or
   (ii) a solid state $^{13}$C NMR having peaks at 18.5, 43.0, 49.9, 52.4, 56.5, 61.9, 115.7, 133.8, 169.1, 171.5 ppm±2 ppm; or
   (iii) combinations of this data.

2. Crystalline form III of Linaclotide according to claim 1 characterized by an X-ray powder diffraction pattern having peaks at 5.1, 7.7, 10.3, 14.8 and 22.0 degrees two theta ±0.2 degrees two theta and also having any one, any two, any three or more additional peaks selected from: 6.3, 9.7, 17.9, 20.6 and 23.4 degrees two theta ±0.2 degrees two theta.

3. Crystalline Form III of Linaclotide according to claim 1 characterized by an X-ray powder diffraction pattern having peaks at 5.1, 7.7, 10.3, 14.8 and 22.0 degrees two theta ±0.2 degrees two theta, and also having any one, any two, any three or more additional peaks selected from: 6.3, 9.7, 17.9, 20.6 and 23.4 degrees two theta ±0.2 degrees two theta and by the absence of peaks at about 8.2 and 16.0 degrees two theta ±0.2 degrees two theta.

4. Crystalline Form III of Linaclotide according to claim 1 characterized by XRD peaks at 5.1, 7.7, 10.3, 14.8 and 22.0 degrees two theta ±0.2 degrees two theta and by the absence of peaks at about 7.2, 8.2, 15.5 and 16.0 degrees two theta ±0.2 degrees two theta.

5. Crystalline Form III of Linaclotide according to claim 1 further characterized by a solid state $^{13}$C NMR spectrum as depicted in FIG. 9.

6. A composition comprising a mixture of Form III of Linaclotide as defined in claim 1, with amorphous form of Linaclotide.

7. A composition comprising Form III of Linaclotide as defined in claim 1.

8. A pharmaceutical composition of Linaclotide prepared by a process comprising combining Form III of Linaclotide as defined in claim 1 with at least one pharmaceutically acceptable excipient.

9. A process comprising converting Form III of Linaclotide as defined in claim 1 to amorphous form of Linaclotide.

10. A process for preparing composition or formulation comprising combining Form III of Linaclotide as defined in claim 1 and at least one pharmaceutically acceptable excipient.

11. A method of treating a subject suffering from gastrointestinal disorders, or otherwise in need of the treatment, comprising administration of an effective amount of a composition as defined in claim 9, to a person in need of the treatment.

* * * * *

SEQUENCE LISTING

```
<160> NUMBER OF SEQ ID NOS: 1

<210> SEQ ID NO 1
<211> LENGTH: 14
<212> TYPE: PRT
<213> ORGANISM: artificial sequence
<220> FEATURE:
<223> OTHER INFORMATION: synthetic peptide Linaclotide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 1

Cys Cys Glu Tyr Cys Cys Asn Pro Ala Cys Thr Gly Cys Tyr
1               5                   10
```